(12) United States Patent
Tsai et al.

(10) Patent No.: US 11,647,737 B2
(45) Date of Patent: May 16, 2023

(54) GENETICALLY MODIFIED RABBIT EXPRESSING AN EXOGENOUS PROTEIN IN MILK

(71) Applicants: APPLIED STEMCELL, INC., Milpitas, CA (US); THE REGENTS OF THE UNIVERSITY OF MICHIGAN, Ann Arbor, MI (US)

(72) Inventors: Ruby Yanru Tsai, San Jose, CA (US); Jie Xu, Fairfax, VA (US); Yuqing Chen, Superior Township, MI (US); Jifeng Zhang, Ann Arbor, MI (US); Ling-Jie Kong, Union City, CA (US)

(73) Assignees: ASC THERAPEUTICS INC., Milpitas, CA (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 787 days.

(21) Appl. No.: 16/475,127

(22) PCT Filed: Dec. 29, 2017

(86) PCT No.: PCT/US2017/068876
§ 371 (c)(1),
(2) Date: Jul. 1, 2019

(87) PCT Pub. No.: WO2018/126095
PCT Pub. Date: Jul. 5, 2018

(65) Prior Publication Data
US 2019/0335729 A1    Nov. 7, 2019

Related U.S. Application Data

(60) Provisional application No. 62/439,896, filed on Dec. 29, 2016.

(51) Int. Cl.
| A01K 67/00 | (2006.01) |
| A01K 67/027 | (2006.01) |
| C07K 14/47 | (2006.01) |
| C12N 9/22 | (2006.01) |
| C12N 15/11 | (2006.01) |
| C12N 15/90 | (2006.01) |

(52) U.S. Cl.
CPC ...... *A01K 67/0278* (2013.01); *C07K 14/4732* (2013.01); *C12N 9/22* (2013.01); *C12N 15/11* (2013.01); *C12N 15/907* (2013.01); *A01K 2217/072* (2013.01); *A01K 2227/107* (2013.01); *A01K 2267/01* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 2009/0013419 A1* | 1/2009 | Han | C12N 15/8509 |
| | | | 435/325 |
| 2012/0124686 A1* | 5/2012 | Luo | C12N 15/8509 |
| | | | 435/462 |
| 2013/0177983 A1 | 7/2013 | Rebar | |

FOREIGN PATENT DOCUMENTS

| WO | WO-2008099077 A2 * | 8/2008 | ............... A23J 1/20 |
| WO | 2009/150477 A2 | 12/2009 | |
| WO | 2013/017555 A1 | 2/2013 | |

OTHER PUBLICATIONS

Song (Nature Comm., 2016, vol. 7, 10548, p. 1-7).*
Encyclopaedia Britannica, 2020, description of Lagomorphs.*
Nogre WO 2008/099077 translation (Year: 2008).*
Jun Song et al: "RS-1 enhances CRISPR/Cas9- and TALEN-mediated knock-in efficiency", Nature Communications, vol. 7, Jan. 28, 2016 (Jan. 28, 2016), p. 10548, XP055342302, DOI: 10.1038/ncomms 10548.
Communication pursuant to Article 94(3) EPC of EP 17888551.3 dated Jan. 10, 2021.
Keown, W. A. et al., "Methods for Introducing DNA into Mammalian Cells", Methods in Enzymology (1990), vol. 185, p. 527-537.
Van Der Putten, H. et al., "Efficient insertion of genes into the mouse germ line via retroviral vectors". Proc. Natl. Acad. Sci. USA(1985), vol. 82, p. 6148-6152.
Thompson, S. et al., "Germ Line Transmission and Expression of a Corrected HPRT Gene Produced by Gene Targeting in Embryonic Stem Cells". Cell(1989), vol. 56, p. 313-321.
Lo, C. W. ,"Transformation by Iontophoretic Microinjection of DNA: Multiple Integrations Without Tandem Insertions". Molecular and Cellular Biology(1983), vol. 3, No. 10, p. 1803-1814.
Lavitrano, M. et al., "Sperm Cells as Vectors for Introducing Foreign DNA into Eggs: Genetic Transformation of Mice". Cell(1989), vol. 57, p. 717-723.
Geurts, A. M. et al., "Knockout Rats via Embryo Microinjection of Zinc-Finger Nucleases". Science(2009),vol. 325, p. 433.
Tesson, L. et al., "Knockout rats generated by embryo microinjection of TALENs". Nature Biotechnology(2011), vol. 29, No. 8, p. 695-696.

(Continued)

*Primary Examiner* — Michael C Wilson
(74) *Attorney, Agent, or Firm* — Jun He Law Offices P.C.; Yi Zhang

(57) ABSTRACT

Provided is a genetically modified non-human mammal that comprises an anchor DNA sequence inserted at an endogenous locus of a secretory milk protein gene, wherein the anchor DNA sequence comprises a site-specific recombinase recognition site. Also provided is a genetically modified non-human mammal that comprises a transgene inserted at an endogenous locus of a secretory milk protein gene, wherein the transgene encodes a secretory protein and is operably linked to the endogenous promoter of said secretory milk protein gene, and wherein the transgene is flanked by a pair of site-specific recombinase resulting sites. The genetically modified non-human mammals provided can be used for producing the secreted recombinant protein encoded by the transgene from the milk produced by the genetically modified non-human mammals.

12 Claims, 4 Drawing Sheets

Specification includes a Sequence Listing.

(56) References Cited

OTHER PUBLICATIONS

Casas, C. et al.,"Massive CA1/2 Neuronal Loss with Intraneuronal and N-Terminal Truncated Aβ42 Accumulation in a Novel Alzheimer Transgenic Model". American Journal of Pathology(2004), vol. 165, No. 4, p. 1289-1300.
Jaenisch, R., "Transgenic Animals". Science(1988), vol. 240, p. 1468-1474.
Braulke, T.et al., "Sorting of lysosomal proteins". Biochimica et Biophysica Acta(2009), 1793(4), p. 605-614.
Srivastava, M. et al., "An Inhibitor of Nonhomologous End-Joining Abrogates Double-Strand Break Repair and Impedes Cancer Progression".Cell (2012), 151(7), p. 1474-1487.
Jayathilaka, K. et al., "A chemical compound that stimulates the human homologous recombination protein RAD51". Proc Natl Acad Sci USA (2008),vol. 105, No. 41, p. 15848-15853.
Xu, Z. et al., "Accuracy and efficiency define Bxb1 integrase as the best of fifteen candidate serine recombinases for the integration of DNA into the human genome". BMC Biotechnology 2013 (Oct. 20, 2013), vol. 13, No. 87, pp. 1-17, abstract.
International Search Report of PCT Application No. PCT/US2017/068876.
Buhler TH A et al: "Rabbit β-Casein Pormoter Directs Secretion of Human Interleukin-2 Into the Milk of Transgenic Rabbits", Biotechnology. The International Monthly for Industrial Biology, Nature Publishing Group, US, vol. 8, No. 2, Feb. 1990 (Feb. 1990), pp. 140-143, XP000087715, ISSN: 0733-222X, DOI: 10.1038/NBT0290-140, p. 140.
Branda C S et al: "Talking about a revolution: The impact of site-specific recombinase on genetic analyses in mice", Cell, US, vol. 6, No. 1, 2004, pp. 7-28, XP002994211, ISSN: 1097-4172, DOI:10.1016/S1534-5807(03) 00399-X, p. 9-p. 10; figure 3.
Nakayama et al: "Homologous recombination in human iPS and ES cells for use in gene correction therapy", Drug Discovery Today, Elsevier, Amsterdam, NL, vol. 15, No. 5-6, Mar. 2010 (Mar. 2010), pp. 198-202, XP026946349, ISSN: 1359-6446, DOI: 10.1016/J.DRUDIS.2010.01.006[retrieved on Jan. 29, 2010], p. 201.
The extended European search report of European application No. 17888225.4, dated Nov. 12, 2020.

* cited by examiner

GENETICALLY MODIFIED RABBIT EXPRESSING AN EXOGENOUS PROTEIN IN MILK

CROSS-REFERENCE TO RELATED APPLICATIONS

This application claims priority to U.S. provisional patent application No. 62/439,896, filed Dec. 29, 2016, the disclosure of which is incorporated herein by reference.

GRANT INFORMATION

This invention was made with Government support under Grant No. GM110822, awarded by the National Institute of Health. The Government has certain rights in this invention.

FIELD OF THE INVENTION

The present invention generally relates to genetically modified non-human mammals. More specifically, the present invention relates to genetically modified non-human mammals comprising a gene encoding a protein that can be secreted via milk, and methods for generating such non-human mammals.

BACKGROUND

Bioproduction is the production of biologics-based therapeutic drugs, e.g., protein-based therapeutics, such as antibodies and vaccines that are so complex that they have to be made in living systems. A variety of processes have been employed for bioproduction, including cultures of microbes, animal cells or plant cells, and purification from natural sources, such as blood and milk. With the combination of transgenic technology, it is possible to generate transgenic animals that secrete target proteins into milk and then purify the target protein from the milk (see, e.g., U.S. Pat. Nos. 7,045,676 and 7,939,317 to Gordon et al.). The advantages of bioproduction from the milk include lower unit cost by 5-50 fold (dollars per gram per protein is 2-20 using milk from animals, compared to 100 using cell culture system), less technical demanding (milk can be produced continuously in the same animal while cell cultures require constant monitoring and sampling), complex protein production (animals naturally carry the cellular mechanisms needed to produce complex proteins, which are difficult, if not impossible to replicate in cell culture) and easy for protein purification from milk (protein is efficiently passed through milk, with an average yield of 53% and with 99% purity). Bioproduction market is growing rapidly in recent years. Examples of transgenic animal bioproduction approved in EU and US include Atryn (antithrombin, manufactured by LBF) expressed in the milk of transgenic goats (approved in Europe in 2006, in the US in 2009) and Ruconest (C1 inhibitor, manufactured by Pharming Group) expressed in the milk of transgenic rabbits (approved in Europe in 2010, and 2016 in the US). Given the increasing demand in therapeutic proteins and the competitions in market sharing, there is a need of improving technologies in bioproduction.

SUMMARY OF INVENTION

In one aspect, the present disclosure provides a genetically modified non-human mammal comprising an anchor DNA sequence inserted at an endogenous locus of a secretory milk protein gene, wherein said anchor DNA sequence comprises a first site-specific recombinase recognition site. In certain embodiments, the anchor DNA sequence further comprises a second site-specific recombinase recognition site. In certain embodiment, the first recombinase recognition site is the same as the second recombinase recognition site. In certain embodiment, the first recombinase recognition site is different from the second recombinase recognition site. In certain embodiments, the first site-specific recombinase recognition site or the second site-specific recombinase recognition site is recognized by a site-specific recombinase selected from the group consisting of Cre, Flp, the lambda integrase, gamma-delta resolvase, Tn3 resolvase, Sin resolvase, Gin invertase, Hin invertase, Tn5044 resolvase, IS607 transposase, Bxb1 integrase, wBeta integrase, BL3 integrase, phiR4 integrase, A118 integrase, TG1 integrase, MR11 integrase, phi370 integrase, SPBc integrase, TP901-1 integrase, phiRV integrase, FC1 integrase, K38 integrase, phiBT1 integrase and phiC31 integrase. In certain embodiments, the first or the second site-specific recombinase recognition site is attP. In certain embodiments, the first or the second site-specific recombinase recognition site is attB. In certain embodiments, the first site-specific recombinase recognition site is phiC31-attP and the second site-specific recombinase recognition site is Bxb1-attP, or vice versa.

In certain embodiments, the secretory milk protein gene is selected from the group consisting of αS1-Casein (CSN1), αS2-Casein, β-Casein (CSN2), κ-Casein, whey acid gene, and α-lactalbumin. In certain embodiment, the secretory milk protein gene is β-Casein. In certain embodiment, the anchor DNA sequence is inserted into intron 1 of the endogenous locus of β-Casein.

In certain embodiments, the anchor DNA sequence further comprises a reporter gene operably linked to the endogenous promoter of said secretory milk protein gene. In certain embodiment, the report gene is flanked by the first and the second site-specific recombinase recognition sites.

In certain embodiment, the non-human mammal is a rodent, such as a rat or a mouse, or a lagomorpha, such as a rabbit, a hare or a pika.

In another aspect, the present disclosure provides a genetically modified non-human mammal. In certain embodiments, the genetically modified non-human mammal comprises a transgene inserted at an endogenous locus of a secretory milk protein gene, wherein said transgene encodes a protein fused with a signal peptide and is operably linked to the endogenous promoter of said secretory milk protein gene, and wherein said transgene is flanked by a first site-specific recombinase resulting site and a second site-specific recombinase resulting site.

In certain embodiments, the first site-specific recombinase resulting site is attR. In certain embodiments, the second site-specific recombinase resulting site is attL. In certain embodiments, the attR is resulted from attP×attB, and the attL is resulted from attB×attP. In certain embodiments, the attL is resulted from attP×attB, and the attR is resulted from attB×attP.

In certain embodiments, the transgene comprises a signal-peptide encoding sequence at its 5' end. In certain embodiments, the transgene comprises a polyA sequence at its 3' end. In certain embodiments, the transgene does not comprise a polyA sequence at its 3' end.

In certain embodiments, the transgene encodes a therapeutic protein selected from the group consisting of antigen binding proteins, antibodies, vaccines, fusion proteins, enzymes, and co-enzymes. In certain embodiments, the transgene is human FVII, or human FX, or human Von Willebrand factor, or human FVIII minetic, or LL37, or Humira. In certain embodiments, the transgene encodes a lysosomal protein, such as alpha-glucosidase with mannose-6 phosphate (M6P) modification. In certain embodiments, the transgene may encodes multiple polypeptides. The sequences encoding the multiple polypeptides may be polycistronic, connected by 2A or IRES sequences.

Also provided herein is a method for making a genetically modified non-human mammal. In certain embodiments, the method comprises inserting an anchor DNA sequence into an endogenous locus of a secretory milk protein gene in an embryo, wherein the anchor DNA sequence comprises a first site-specific recombinase recognition site; transferring the embryo to a female mammal of the same species; and allowing said embryo to develop into an animal.

In certain embodiments, the inserting step comprises introducing into the embryo a gene-editing enzyme selected from the group consisting of a ZFN, a TALEN, and a CRISPR/Cas. In certain embodiments, the gene-editing enzyme is a CRISPR/Cas and the inserting step further comprises introducing to the embryo a sgRNA designed for the target sequence of the endogenous locus. In one example, the sgRNA has a sequence of:

GGATATCATGTTAGAGTGCCTGG. (SEQ ID NO: 1)

In certain embodiments, the inserting step comprises treating the embryo with a homology directed repair (HDR) enhancer. In certain embodiments, the homology directed repair (HDR) enhancer is RS-1. In certain embodiments, the embryo is treated with RS-1 of about 7.5 µM for about 20 hours.

Also provided herein is a method for making a genetically modified non-human mammal. In certain embodiments, the method comprises obtaining an embryo derived from a non-human mammal, wherein the embryo comprises an anchor DNA sequence inserted at an endogenous locus of a secretory milk protein gene, wherein said anchor DNA sequence comprises a first site-specific recombinase recognition site recognized by a site-specific recombinase; introducing to the embryo a construct which comprises a transgene encoding a protein or peptide and a second site-specific recombinase recognition site recognized by the site-specific recombinase, and the site-specific recombinase, wherein the site-specific recombinase mediates the recombination between the first and the second site-specific recombinase recognition sites, thereby inserting the transgene at the endogenous locus of the secretory milk protein gene, wherein the transgene is operably linked to the promoter of the secretory milk protein gene; transferring the embryo carrying the transgene to a female host mammal of the same species; and allowing said embryo to develop into an animal.

In certain embodiments, the non-human mammal is capable of producing the protein encoded by the transgene and secreted the protein in milk.

Also provided herein is a method for making a secretory protein. In certain embodiments, the method comprises inducing lactation in the genetically modified non-human mammal provided herein, a genetically modified non-human mammal generated by the method provided herein, or genetically modified progeny of said non-human mammal, wherein the progeny's genome comprises said gene modification; collecting said secretory protein from said collected milk.

DESCRIPTION OF THE INVENTION

Figure 1:
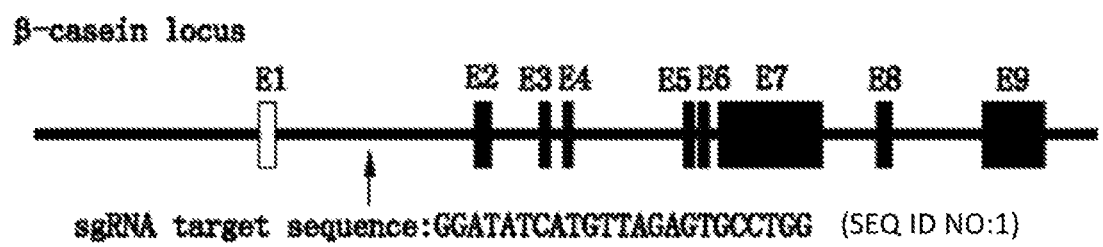
FIG. 1 shows a schematic of the rabbit CSN2 (β-Casein) gene (not to scale) locus which consists of 9 exons (E1-E9), while the first coding Exon is E2. The sgRNA targeting sequence in the CSN2 (β-Casein) gene for CRISPR/Cas9 mediated gene targeting is also illustrated.

We have developed several kinds of genetically modified non-human mammals for bioproduction. In one aspect, the mammal comprises an anchor DNA sequence inserted at an endogenous locus of a secretory milk protein gene, wherein the anchor DNA sequence comprises a site-specific recombinase recognition site. The mammal can be used as a founder animal for genetic engineering to introduce target transgene to the endogenous locus of the secretory milk protein gene. Hence in another aspect, the mammal comprises a transgene inserted at an endogenous locus of a secretory milk protein gene, wherein the transgene encodes a secretory protein and is operably linked to the endogenous promoter of said secretory milk protein gene, and wherein the transgene is flanked by a pair of site-specific recombinase resulting sites. The genetically modified non-human mammals provided can be used for producing the secreted recombinant protein encoded by the transgene from the milk produced by the genetically modified non-human mammals. These and other aspects of the disclosure are discussed below.

Definition

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The term "anchor gene" or "anchor DNA sequence" as used herein refers to a nucleotide sequence that, when being inserted into the genome of an animal, can be used to facilitate the insertion of a transgene of interest. In certain embodiments, an anchor gene comprises a site-specific recombinase recognition site. In certain embodiments, an anchor gene can further comprises a reporter gene. In certain embodiments, the anchor gene can be introduced into the genome via homologous recombination.

The term "introduce" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The vector of the present disclosure may be introduced into a cell using any method known in the art. Various techniques for transforming animal cells may be employed, including, for example: microinjection, retrovirus mediated gene transfer, electroporation, transfection, or the like (see, e.g., Keown et al., Methods in Enzymology 1990, 185:527-537). In one embodiment, the vector is introduced to the cell via a virus.

The term "non-human mammal" as used herein refers to a mammal, except human being, at any stage of development. In certain embodiments, the non-human mammal is a rodent, a mouse, a rat, a rabbit, a monkey, a dog, a cat, a sheep, cattle, a primate, and/or a pig. In some embodiments, the non-human mammal may be a transgenic mammal, genetically-engineered mammal, and/or a clone. In certain embodiments, the non-human mammal is highly efficient in inducing a process of involution and cessation of milk production in a mammary gland of a lactating mammal, including a lactating livestock animal.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

As used herein, a "promoter" is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

The term "recombination" refers to a process of exchange of genetic information between two polynucleotides. "Homologous recombination (HR)" refers to the specialized form of an exchange that takes place, for example, during repair of double-strand breaks in cells. Nucleotide sequence homology is utilized in recombination, for example using a "donor" molecule to template repair of a "target" molecule (i.e., the one that experienced the double-strand break) and is variously known as "non-crossover gene conversion" or "short tract gene conversion," because it leads to the transfer of genetic information from the donor to the target.

A "secretory milk protein gene" or "milk protein gene" refers to the genes encoding caseins (see U.S. Pat. No. 5,304,489), beta-lactoglobulin, alpha-lactalbumin, and whey acidic protein. In certain embodiments, the casein gene is preferred, for example, αS1-Casein (CSN1), αS2-Casein, β-Casein (CSN2), or α-Casein. The transcription promoter from a milk protein gene is used to obtain expression in the mammary gland the protein of interest. In certain embodiments, the anchor gene is operably linked to the promoter of a milk protein gene at the endogenous locus of said milk protein gene, or at a different site in the genome other than the endogenous locus, such as a safe harbor locus, e.g. Hipp11 (H11) locus, ROSA26 locus, Rosa26 like locus (LLC), HPRT, AAVS1 or multiple antibiotic resistance (mar) locus.

As used herein, a "selectable marker" refers a gene whose expression in cells allows the cells to be enriched or depleted under particular culture conditions. A selectable marker may be a foreign gene or a cellular gene which is not naturally expressed or such a gene which is naturally expressed, but at an inappropriate level, in the target cell populations.

"Site-specific recombinase" as used herein refers to a family of enzymes that mediate the site-specific recombination between specific DNA sequences recognized by the enzymes. Examples of site-specific recombinase include, without limitation, Cre recombinase, Flp recombinase, the lambda integrase, gamma-delta resolvase, Tn3 resolvase, Sin resolvase, Gin invertase, Hin invertase, Tn5044 resolvase, Tn3 transposase, sleeping beauty transposase, IS607 transposase, Bxb1 integrase, wBeta integrase, BL3 integrase, phiR4 integrase, A118 integrase, TG1 integrase, MR11 integrase, phi370 integrase, SPBc integrase, SV1 integrase, TP901-1 integrase, phiRV integrase, FC1 integrase, K38 integrase, phiBT1 integrase and phiC31 integrase.

In certain embodiments, the site-specific recombinase is a uni-directional recombinase. As used herein, "uni-directional recombinases" refer to recombinase enzymes whose recognition sites are destroyed after recombination has taken place. In other words, the sequence recognized by the recombinase is changed into one that is not recognized by the recombinase upon recombination mediated by the recombinase, and the continued presence of the recombinase cannot reverse the previous recombination event.

In certain embodiments, the expression of the integrase/site-specific recombinase can be achieved by inserting the integrase/recombinase gene into the genome of a cell, such as introducing an integrase/site-specific recombinase gene-containing vector (including promoters and other elements for expression) into the host cell so that integrase/recombinase can be expressed in the cell. Alternatively, the expression of the integrase/site-specific recombinase can be achieved by introducing into the cell the integrase/recombinase protein, mRNA or a plasmid containing the integrase/recombinase gene.

The term "vector" as used herein refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, nanoparticles, protein coating or the like.

DNA Construct and Vector

In one aspect, the present disclosure provides a DNA construct or vector, e.g., a donor plasmid or an oligodeoxyribonucleotides (ODN), that comprises an anchor gene for the purposes of gene integration in animal genome. In certain embodiments, the anchor gene is flanked by 5' and 3'homology arms of a secretory milk protein gene sequence, e.g. β-Casein (CSN2). The 5' and 3'homology arms are cloned, e.g. by PCR, from the milk protein gene sequence, or by de novo DNA synthesis based on the location of insertion.

In certain embodiments, the anchor gene comprises a single site-specific recombinase recognition site. In certain embodiments, the anchor gene comprises two site-specific recombinase recognition sites. The two site-specific recombinase recognition sites can be the same or different. In certain embodiments, the anchor gene comprises a reporter gene that is flanked by said two site-specific recombinase recognition sites, e.g., PhiC31 attP site at the 5' and Bxb attP site at the 3' to facilitate uni-directional cassette exchange of transgenes. In certain embodiments, the recombination sites are selected from the group consisting of wild-type attB, wild-type attP, pseudo-site thereof, and tandem repeats thereof In certain embodiments, the anchor gene further comprises a splicing acceptor (SA) signal after the first attP site to make the reporter gene spliced in fusion to exon1 of a milk protein mRNA. This will also leave the first attP site in the intron therefore spliced out and will not be in the fusion mRNA. In certain embodiments, the reporter gene with a signal peptide sequence at its 5' and a polyA signal at its 3' to make secreted protein encoded by the reporter gene. In certain embodiments, the reporter gene is not operably linked to a polyA signal at its 3'.

In certain embodiments, the vector further comprises a selectable marker. As used herein, a "selectable marker" refers a gene whose expression in cells allows the cells to be enriched or depleted under particular culture conditions. A selectable marker may be a foreign gene or a cellular gene which is not naturally expressed or such a gene which is naturally expressed, but at an inappropriate level, in the target cell populations.

If the expression of the gene allows the cells to be enriched under particular conditions, the selectable marker is a "positive selectable marker." Typically, a positive selectable marker is a gene that encodes for antibiotic resistance and selecting for those cells that express the selection marker comprises introducing antibiotic into the culture. In use, application of the antibiotic selectively kills or ablates cells that do not express the marker, leaving behind a population of cells purified or enriched in respect of those expressing the antibiotic resistance. Examples of a positive selectable marker include aminoglycoside phosphotransferase (neomycin resistance gene), puromycin-N-acetyl transferase (puromycin resistance gene), hygromycin resistance gene, and blasticidin S deaminase (blasticidin S resistance gene). Other examples of positive selectable marker include genes that can be used to select through cell sorting, e.g., fluorescent proteins and cell surface markers.

Conversely, if the expression of the gene allows the cells to be depleted under particular culture condition, the selectable marker is a "negative selectable marker."Examples of a negative selectable marker include thymidine kinase gene. In use, application of ganciclovir kills the cells with expression of thymidine kinase. Other examples of negative selectable markers include DT toxin, cell death genes, such as TRAIL, caspases and BCL2 family genes.

Master Transgenic Mammals

In another aspect, the present disclosure provides a master or parental non-human transgenic mammal that comprises in its germline the anchor gene described herein. In certain embodiments, the non-human transgenic mammal can be generated by introducing the construct containing the anchor gene into the genome of a pluripotent cell or an embryo of a non-human mammal. In certain embodiments, the introduction of anchor gene can be introduced into an animal by any method known to those skilled in the art. The sequence of the desired anchor gene can be introduced into pluripotent cells, such as zygotes or embryonic stem (ES) cells, by any method that will permit the introduced molecule to undergo recombination at its regions of homology. Techniques that can be used include, but are not limited to, calcium phosphate/DNA co-precipitates, microinjection of DNA into the pronucleus or cytoplasm of one-cell embryos, electroporation, bacterial protoplast fusion with intact cells, transfection, retroviral infection, and polycations, (e.g., polybrene, polyornithine, etc.), retrovirus mediated gene transfer into germ lines (Van der Putten et al., Proc. Natl. Acad. Sci. USA 82:6148-6152 (1985)), gene targeting in embryonic stem cells (Thompson et al., Cell 56:313-321 (1989)), electroporation of embryos (Lo, Mol. Cell. Biol. 3:1803-1814 (1983)), and sperm-mediated gene transfer (Lavitrano et al., Cell 57:717-723 (1989)). In certain embodiments, the DNA is single or double stranded DNA, linear or circular. (See for example, U.S. Pat. No. 4,873,191; Geurts et al., "Knockout Rats via Embryo Microinjection of Zinc-Finger Nucleases," Science, vol. 325, p. 433 (Jul. 24, 2009); Tesson et al., "Knockout rats generated by embryo microinjection of TALENs," Nature Biotechnology, vol. 29, No. 8, pp. 695-696 (Aug. 2011); Hogan et al., Manipulating the Mouse Embryo: A Laboratory Manual Cold Spring Harbor Laboratory (1986); Casas et al. (2004) Am J Pathol 165, 1289-1300; Hogan et al., Manipulating the Mouse Embryo: A Laboratory Manual, second ed., Cold Spring Harbor Laboratory (1994); U.S. Pat. Nos. 5,602,299; 5,175,384; 6,066, 778; 4,873,191 and 6,037,521).

The standard microinjection involves isolating fertilized ova, visualizing the embryos, injecting the DNA into either the pronucleus or the cytoplasm while holding the ova at a blunt holding pipette (a diameter of about 50 μm), injecting a mixture of gene modification components including DNA, RNA, mRNA, or protein, or ribonucleoprotein (RNP), small molecule, buffer, and etc. into the pronucleus or cytoplasm using a sharply pointed pipette with a diameter of about 1.5 μm.

Embryonic cells at various developmental stages, such as embryonic stem (ES) cells, can also be used to introduce genes for generating transgenic animals. Different methods are utilized depending on the stage of development of the embryonic cell. Those transfected embryonic cells can then colonize an embryo after their introduction into the blastocoele of a blastocyst-stage embryo and contribute to the germ line of the resulting chimeric animal (see in detail: Jaenisch, Science 240:1468-1474 (1988)). Together with the transgene construct, in certain embodiments, a Cas9 mRNA and sgRNA targeting the milk protein gene, e.g. β-casein (CSN2), are also transfected into the above embryonic cells to allowing site-specific insertion of the transgene into the endogenous locus of the milk protein gene. The sequence of sgRNA is designed according to the recombination sites, for example, Intron 1 or Exon 2 of (β-casein gene. A skilled artisan will appreciate, in addition to CRISPR/Cas system, other systems facilitating the knock-in process can be used, such as ZFN and TALEN. In certain embodiments, a homology directed repair (HDR) enhancer, such as RS-1, is added to the embryonic cells to increase the knock-in efficiency of nuclease mediated gene targeting system, e.g. CRISPR/Cas or TALEN.

Prior to the introduction of transfected embryonic cells into the blastocyst, the transfected embryonic cells can be subjected to various selection protocols to enrich the proportion of embryonic cells that have integrated the knock-in gene if the knock-in gene provides a means for such selection. In certain embodiments, the donor plasmid/ODN contains negative selection marker, such as diptheria toxin A (DTA) or HSV-TK, to reduce the non-specific random insertion of the DNA fragment of the anchor gene. Alternatively, PCR can be used to screen for embryonic cells that have integrated the knock-in.

Other pluripotent cells include a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell.

A mammalian cell can be a livestock cell, such as a cow, a sheep, a goat or a pig cell. A mammalian cell can also be a rodent cell, e.g., a mouse, rat, hamster cell. In certain embodiments, a mammalian cell can be a lagomorpha cell, e.g., a rabbit cell. A mammalian cell can also be a non-human primate cell, e.g., simians, monkeys, apes, and prosimians.

The embryo carrying the transgenes are then transferred into a female host mammal of the same species to allow said embryo to develop into an animal. The resulting animal are screened and evaluated to select those animals having the transgenes in their genome. The transgenic animal carrying the transgene in their genome can be used as the master animal for further gene replacement with gene of interest.

The transgenic animals can be bred, inbred, outbred, or crossbred to produce animals with the transgene. Examples of such breeding strategies include, but are not limited to: breeding of transgenic animals with more than one integration site to establish separate lines; breeding of separate lines in order to produce compound transgenics that express the transgene at higher levels because of the effects of additive expression of each transgene; crossing of heterozygous transgenic mice to produce homozygous animals for a given integration site in order to both augment expression and eliminate the need for screening of animals by DNA analysis; crossing of separate homozygous lines to produce compound heterozygous or homozygous lines; breeding animals to different genetic strain backgrounds so as to examine effects of modifying alleles on expression of the transgene and the effects of expression.

Transgenic animals having transgenes at different sites can also be cross bred to generate lines with different transgenes. For example, a transgenic animal carrying a transgene at the endogenous locus of β-Casein can be bred with a transgenic animal carrying a transgene at the endogenous locus of αS1-Casein (CSN1), so that offspring carrying transgenes at both the endogenous loci of (β-Casein and αS1-Casein can be produced.

Gene Replacement and Pharming Mammals

In yet another aspect, the present disclosure provides a pharming non-human transgenic mammal for purposes of bioproduction that comprises in its germline a target transgene inserted to the endogenous secretory milk protein gene. In certain embodiments, pharming transgenic mammal is generated by replacing the anchor gene in the germline of the master mammal with the target tansgene. In certain embodiments, the anchor gene inserted at the endogenous locus of a secretory milk protein gene can be replaced with the transgene of interest, so that the gene of interest can be operably linked to the promotor of the secreted milk protein gene. To integrate said transgene of interest at the anchoring site, a targeting construct is introduced into the cells, such as an embryo of the master animal. The targeting construct contains the transgene of interest flanked by one or two attB (or attP) sites, when the anchor gene comprises one or two attP (or attB) sites, respectively.

In certain embodiments, site-specific recombinase, such as serine integrase is introduced into said cells as plasmid vector, or mRNA or protein. The serine integrase mediates the recombination between the attP and attB sites. In one possibility, the recombination occurs between one attP and one attB site. In such case, the transgene is inserted at one anchoring site. In a second possibility, the recombination occurs between two pairs of attP and attB sites, resulting in the swap of the sequence in between the two attP (or attB) sites with the gene of interest. In a third possibility, the recombination between two pairs of attP and attB sites results in the swap of the sequence in between the two attP (or attB) sites with the backbone of the target construct.

In certain embodiments, the targeting construct contains the transgene of interest flanked by two different attB (or attP) sites, each recognized by a different site-specific recombinase, and the anchor gene comprises two different attP (or attB) sites, respectively. To mediate the recombination, the two site-specific recombinases are introduced into the cell. Each site-specific recombinase mediates the recombination between one pair of attP and attB. As a result, the anchor gene is replaced through recombination by the transgene of interest in a directional manner, eliminating the possibility that the backbone of the targeting construct is inserted to the target locus.

Following the gene replacement at the endogenous locus of the secreted milk protein gene, the embryos are transferred into recipient female animal of the same species to develop into an animal.

In certain embodiments, an integrase-resulting site is the sequence resulting from the recombination of two corresponding integrase-specific sites. For example, an integrase-resulting site is attL or attR. The attL and attR sites are results of recombination of the attP and attB sites.

In certain embodiments, the replaced gene encodes a non-native polypeptide. In certain embodiments, the replaced gene encodes a recombinant protein that usually is not secreted into the milk. In certain embodiments, the replaced gene encodes a therapeutic protein selected from the group consisting of antigen binding proteins, antibodies, vaccines, fusion proteins, enzymes, co-enzymes, polycistronic, and multiple peptides connected by 2A or IRES sequences, or the homologous thereof. Examples of the therapeutic proteins include, but not limited to, proteins selected from the group consisting of: LL37, alpha-1 antitrypsin, angiostatin, antihemolytic factor, antibody, antibody fragments, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, clotting Factor IX, Factor VII, Factor VIII, Factor X, Von Willebrand factor, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor 1, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone, lysosomal proteins such as soluble acid hydrolases (e.g., glycosidases, proteases, lipases, nucleases, phosphatases, and sulfatases) and lysosomal membrane proteins, as described in detail by T. Braulke and J. S. Bonifacino, "Sorting of lysosomal proteins" Biochimica et Biophysica Acta, Volume 1793, Issue 4, Pages 605-614 (April, 2009).

Upon obtaining the genetically modified mammal carrying the transgene that is operably linked to the endogenous promoter of secreted milk protein gene in the mammary glands, the female transgenic mammals, or their progenies having the modified genome are induced lactation. The genetically modified mammals can produce secreted recombinant protein into the milk, which can be collected and purified from the milk.

EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Design of sgRNAs for CRISPR/Cas

Effective sgRNAs are designed for targeting the rabbit CSN2 (i.e. β-Casein) gene. Rabbit CSN2 (rbCSN2) gene is located on Chromosome 15, consisting of 9 exons. The first coding Exon is Exon 2. The gene organization is illustrated in FIG. 1

To conserve endogenous control elements of CSN2, with the goal to achieve high expression level of the transgene, we designed sgRNAs targeting the intron 1 sequence. The particular sequence selected from intron 1 on the sense strand is shown as SEQ ID NO:2.

We next subjected the selected sequence to the online CRISPR design site (crispr.mit.edu). Four possible guide sequences were selected based on its predicted activity and safety profiles.

Example 2: In Vitro Validation of sgRNAs

Figure 2:
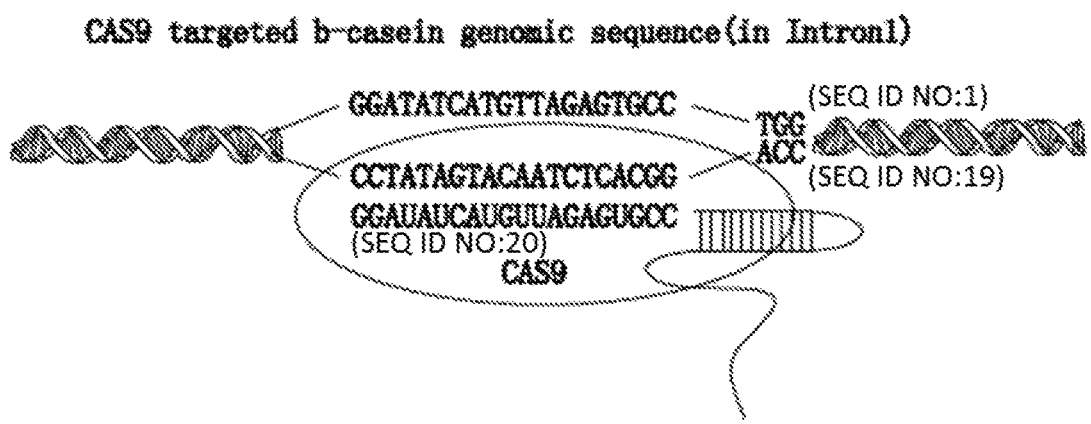
FIG. 2 illustrates the working mechanism for CRISPR/Cas9 in targeting the β-casein gene

We next performed in vitro experiments to validate the effectiveness of designed sgRNAs. The possible guide sequences were tested for activity by surveyer assay and gRNA #3 was finally chosen based on its activity and safety profile (FIG. 2).

Figure 3:
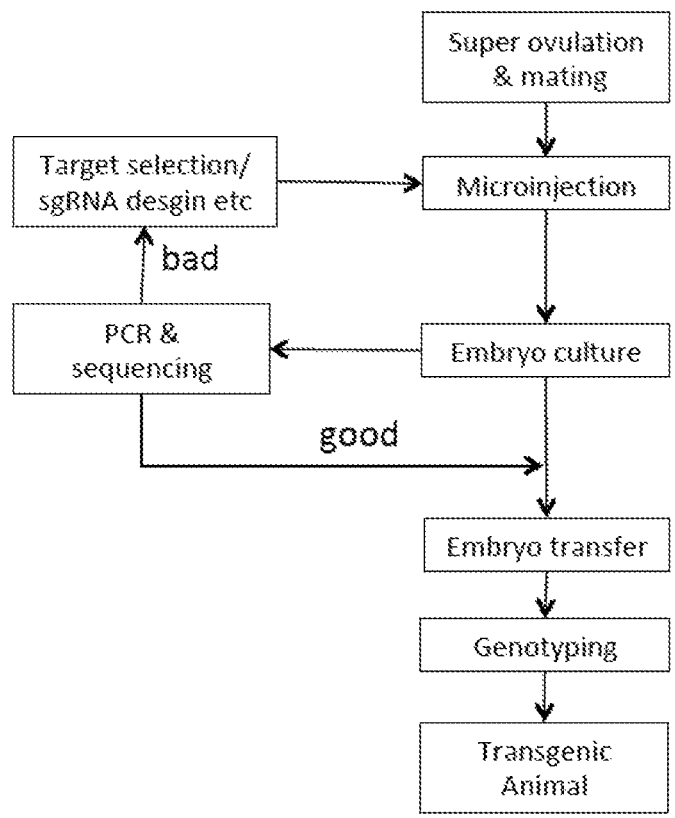
FIG. 3 illustrates the scheme for in vitro validation and in vivo production process of transgenic animal bioproduction.

The overall process and decision points are illustrated in FIG. 3. sgRNA #3 was used for in vivo production of transgenic animals.

TABLE 1 sgRNAs targeting rabbit β-Casein

| | Sequence |
|---|---|
| Targeted sequence | SEQ ID NO: 2 |
| sgRNA #1 | GGTCCTCATTCTCGCCTGCCTGG (SEQ ID NO: 3) |
| sgRNA #2 | GGTGGCTCTCGCTCTTGCAAGGG (SEQ ID NO: 4) |
| sgRNA #3 | GGATATCATGTTAGAGTGCCTGG (SEQ ID NO: 1) |
| sgRNA #4 | GGGGTTAGGGAGTAGGCAAGAGG (SEQ ID NO: 5) |
| sgRNA #7 | CCTCATTCTCGCCTGCCTGG TGG (SEQ ID NO: 18) |

All animal maintenance, care and use procedures were reviewed and approved by the University Committee on the Use and Care of Animals (UCUCA) of the University of Michigan. Embryos were harvested from superovulated embryo donor female rabbits as previously described. Microinjection was performed on embryos 19-21 h post insemination using a micromanipulator under the inverted microscope equipped with a differential interference contrast (DIC) device. A mixture containing 100 ng/μl Cas9 mRNA and 6 ng/μl sgRNA were used for cytoplasmic microinjection. The injected embryos were washed and cultured in vitro for 3-4 days until they reached blastocyst stage.

Figure 4:
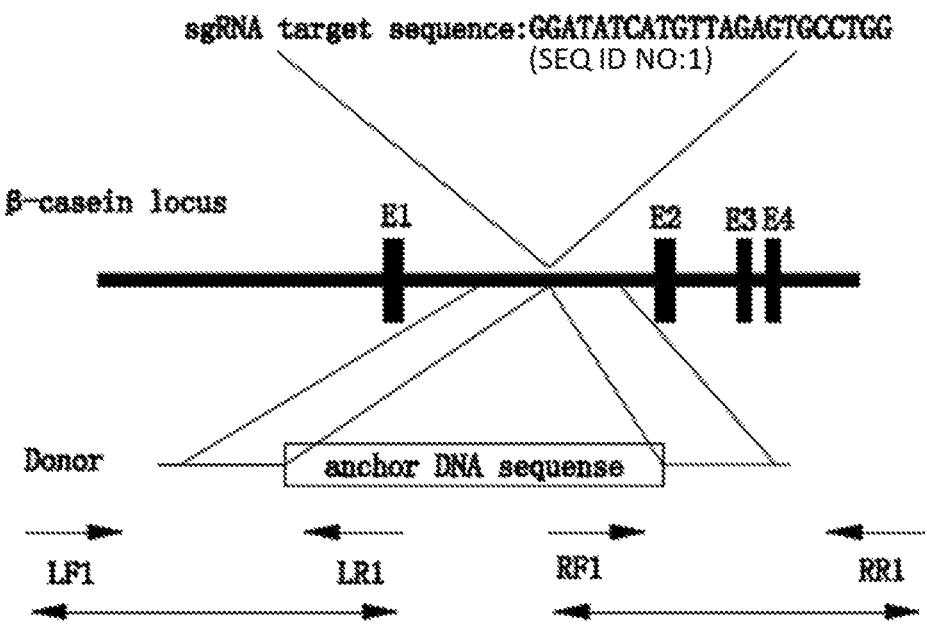
FIG. 4 illustrates the gene targeting strategy and primers for genotyping knockout and knock-in events. Primer set LF1/RR1 is used for confirming knockout events, and for in vitro detection of presumptive knock-in events. Primer sets LF1/LR1 and RF1/RR1 are to be used to confirm accurate knock-in events in founders and their offspring animals.

Blastocyst stage embryos were lysed individually and genomic DNA extracted. To get better PCR reaction, the whole genome was replicated using a REPLI-g® Mini Kit (Qiagen, Germantown, Md.) following the manufacturer's protocol with slight modification. PCR products using primer set LF1/RR1 were purified and sequenced for detection of indel mutations proximate to the sgRNA target sequence (FIG. 4). On the chromatographic curves, peaks on peaks approximate the targeting site indicate an indel event. Mutation Surveyor (Softgenetics, State College, Pa.) was used to analyze sequencing results.

TABLE 2

In vitro validation of sgRNAs

| Target gene | No. embryos microinjected | No. Blastocyst (%) | Genotyped by sequencing | #mutated (%) | Bi-allelic mutations (%) |
|---|---|---|---|---|---|
| β-casein | 102 | 59 (58) | 56 | 35 (63) | 12 (36) |
| αs1-casein | 88 | 37 (42) | 37 | 22 (59) | 5 (23) |

In total, we performed microinjection to 102 pronuclear stage embryos with sgRNA#3 targeting β-casein (rbCSN2) (see Table 1). Satisfactorily, 63% of all blastocysts (n=56) that were PCR and sequenced contained insertions or deletions at or proximate the targeted cleavage site; 36% (n=12) contained biallelic mutations. These results confirmed that sgRNA#3 is effective in targeting rbCSN2.

Because αs1-casein (rbCSN1) represents another potential knock-in locus for mammary gland production of biotherapeutic agents, we designed sgRNAs targeting rbCSN1. 59% indel and 23% bi-allelic mutation rates were achieved, again confirming the high efficiency of this sgRNA.

TABLE 3 sgRNAs targeting rabbit αs1-Casein

| | sequence |
|---|---|
| Targeted sequence | CCATCGCCTAGATCATCAACCCAACTTGCCTCTTTTCAGT CGAGTTTAAGG (SEQ ID NO: 6) |
| Guide #1 | TCGACTGAAAAGAGGCAAGT TGG (SEQ ID NO: 7) |
| Guide #2 | GCAAGTTGGGTTGATGATCT AGG (SEQ ID NO: 8) |
| Guide #3 | CGACTGAAAAGAGGCAAGTT GGG (SEQ ID NO: 9) |

Example 3: Construction of Donor DNA

The goal of the present study is to modernize the existing animal pharming process. In particular, we proposed to generate master transgenic rabbits that: (i) can produce pharmaceutical proteins at a level of >10 g/L by utilizing the endogenous major milk protein (e.g., β-casein, αs1-casein) expression elements; (ii) can be efficiently (>40%) converted to express another pharmaceutical protein product in a "cassette exchange manner" taking advantage of the pre-deposited integrase sequences.

Figure 5:
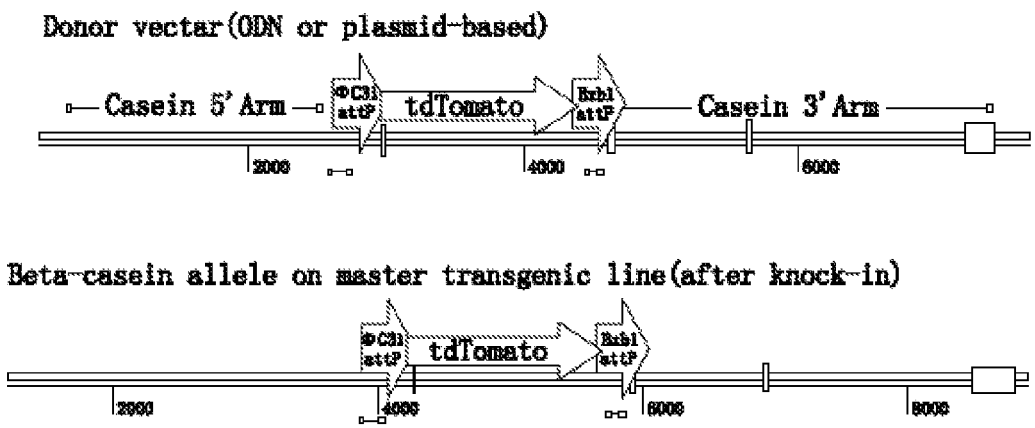
FIG. 5 illustrates the gene targeting construct with the 5' and 3' arms of casein gene sequence flanking the anchor gene (e.g., tdTomato) and integrase-recognition sites of phiC31 attP and Bxb 1 attP. The lower panel shows the transgene after knock-in at the endogenous rabbit β-Casein locus.

Towards these features, we designed the donor DNA vector as illustrated in FIG. 5. The transgene (i.e., tdTomato) is immediately flanked by PhiC31 and Bxb1 integrase sequences (e.g., phiC31-attP and bxb1-attP) and next by homology arms to the rbCSN2 sequences.

The transgene are expressed under beta-casein promoter. Based on the location of gRNA3, the 1.5 kb 5' arm and 3' arms were cloned by PCR of rabbit genomic DNA. The insert DNA fragment between 5' and 3' arms includes following components:

i. PhC31 attP site at the 5' and Bxb1 attP site at the 3' to facilitate uni-directional transgene replacement.
  ii. A splicing acceptor (SA) signal after the 1st attP site to make the transgene spliced in fusion to exon1 in the mRNA. This will also leave the 1st attP site in the intron and will not be in the mRNA.
  iii. The td-tomato reporter gene with a signal peptide sequence at its 5' and a polyA signal at its 3' to make secreted td-tomato protein.

The donor plasmid also contains DTA selectable marker to reduce the non-specific random insertion of the trans DNA fragment.

Example 4: Improvement of Nuclease Mediated Knock-In Efficiency in Rabbit Embryos A major technical challenge in achieving the proposed goals is the low knock-in efficiency in rabbits, even with the use of CRISPR/Cas9. Non-homologous end joining (NHEJ) and homology directed repair (HDR) are the two main DNA repair mechanisms after Cas9/TALEN/ZFN cleaves the DNA at the target site, where NHEJ would lead to knock-out (KO) characterized by unpredictable indels and HDR favors the knock-in events when a donor template vector is co-introduced. To test whether inhibiting NHEJ or enhancing HDR will increase the chance of knock-in events in the nuclease mediated gene targeting system, we conducted experiments to examine the effects of a potent NHEJ inhibitor, SCR7 (Srivastava Metal., Cell (2012) 151(7):1474-87), and an HDR enhancer, RS-1, i.e., 3-[(benzylamino)sulfonyl]-4-bromo-N-(4-bromophenyl)benzamide (Jayathilaka K et al., Proc Natl Acad Sci USA (2008) 105(41):15848-53) on improving the efficiency of Cas9 or TALEN mediated HDR in rabbit embryos.

Figure 6:
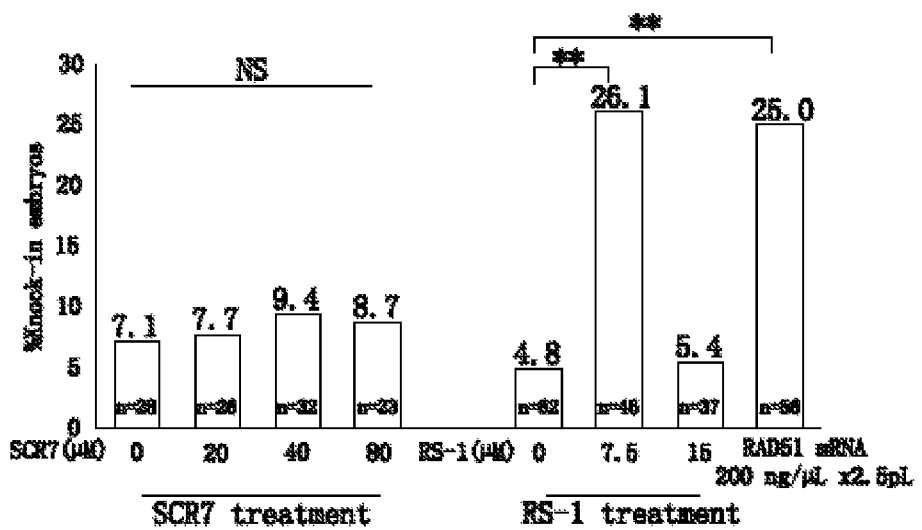
FIG. 6 illustrates the improvement of Cas9 or TALEN mediated HR efficiency in rabbit embryos with treatment of HDR enhancer. Effects of SCR7, RS-1, or RAD51 mRNA in improving Cas9 mediated HR efficiency at rabbit Rosa26 like locus (RLL).
Figure 7:
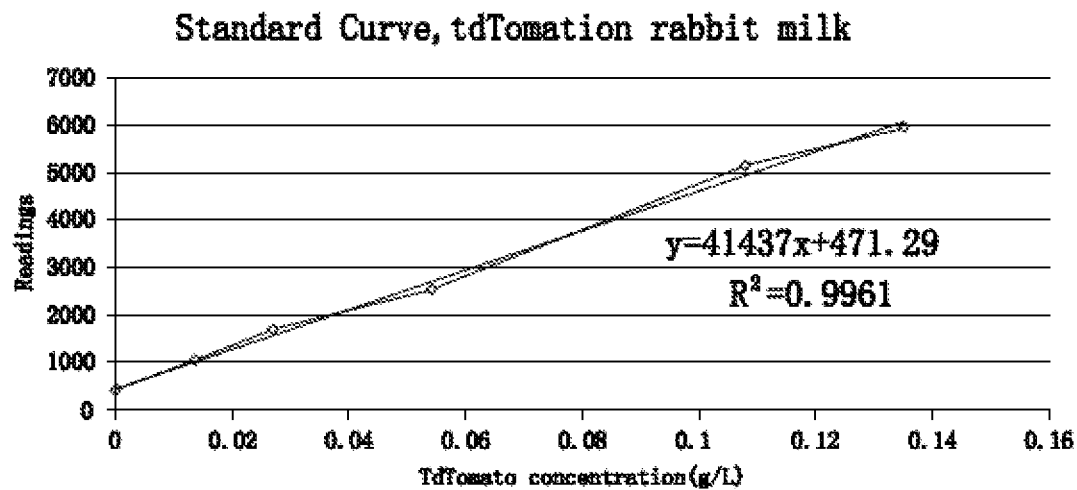
FIG. 7 illustrates the high yield of recombinant protein in the milk of pharming rabbit. In the founder rabbits, a recombinant tdTomato as a reporter expression cassette is driven by the endogenous beta-casein promoter. The founder rabbits were bred to generate female heterozygous MRP1.0-DSR rabbit. And the tdTomato concentration in the milk from this animal was determined. The tdTomato concentration was measured to be 6.3 g/L. The tdTomato concentration in a homozygous MRP1.0-DSR female reached 12.5 g/L.

We first tested the effects of SCR7 and RS-1 on Cas9 mediated HDR at a ROSA26 like locus (RLL) in the rabbit genome (FIG. 6). Donor template DNAs were co-microinjected with Cas9 mRNA and sgRNA for RLL locus. After injection, the embryos were treated for 20 h in a serial concentration of SCR7: 0 μM (control), 20 μM, 40 μM, and 80 μM, or in RS-1 at 0 μM (control), 7.5 μM, and 15 μM. Treating embryos with SCR7 at these conditions had no significant effects on the overall knock-in efficiency (7.1% in the control vs. 7.7-9.4% in the treatment groups). Treating embryos with RS-1 at 7.5 μM, surprisingly, resulted in 26.1% (12 out of 46) knock-in rate, significantly higher than those of control (4.8%) and at 15 μM (5.4%). Interestingly, microinjecting RAD51 mRNA mimicked the beneficial effects of RS-1, further confirming that RAD51 is the target of RS-1 for improving nuclease mediated HDR efficiency.

Example 5: In Vitro Knock-In Efficiencies to the Beta-Casein Locus

After confirming the in vitro efficacy of the sgRNA (Example 2), and the improvement of the knock-in efficiency (Example 4), we evaluated the efficiencies of generating td-Tomato knock-in embryos. A mixture containing 100 ng/μl donor DNA, 100 ng/μl Cas9 mRNA and 6 ng/μl sgRNA were used for cytoplasm microinjection. Embryos were subsequently cultured to blastocyst stages, genomic DNA extracted, and subjected to PCR using primer sets described in FIG. 4. Embryos that are positive containing the desired band size for both primer sets LF1/LR1 and RF1/RR1 are considered putative knock-in.

Consistent with data presented in Example 4, application of RS-1 at 7.5 µM significantly increased the knock-in rates, from 8.3% to 28.9% (P<0.05) (see Table 2).

TABLE 4

Knock-in rates in rabbit embryos.

| | Embryo injected | Blastocysts (%) | Sequenced | Putative KI | % KI |
|---|---|---|---|---|---|
| Control | 60 | 24 | 24 | 2 | 8.3 |
| RS-1 | 135 | 69 | 69 | 20 | 28.9 |

Example 6: Embryo Transfer Results

After in vitro validation of the knock-in rates as described in Example 5, embryo transfer step was conducted with the goal to produce knock-in founder rabbits.

After microinjection, embryos were cultured overnight (20 hours) with RS-1 treatment, before surgically transferred into the oviduct of a synchronized recipient doe. Approximately fifteen to twenty embryos were transferred to one recipient doe. The results were summarized in Table 3 below. In short, we transferred 45 embryos into 3 recipients. Two out the three recipients were pregnant and gave rise to 9 kits total. Among these kits, two were found to have knock-in of the transgene.

TABLE 5

Production of Founder Rabbits Containing Anchor Transgene

| No. of embryos transferred | No of recipients | No of pregnant | No of kits born | No of knock-in kits (%) | No of male founder | No of female founder |
|---|---|---|---|---|---|---|
| 45 | 3 | 2 | 9 | 2 (22) | 1 | 1 |

The knock-in kits were bred to generate offspring with homozygous knock-in, as shown in Table 4.

TABLE 6

Germline transmission and herd establishment of master rabbits

| Generation | No of kits born | No of heterozygous knock-in kits | No of homozygous knock-in kits |
|---|---|---|---|
| F1 | 8 | 2 | 0 |
| F2 | 7 | 23 | 3 |

Example 7. Production of Recombinant Protein in Master Transgenic Rabbits

We then measured the yield of recombinant tdTomato (as a reporter) in the milk of master rabbits. In the master rabbits, a recombinant tdTomato expression cassette is driven by the endogenous beta-casein promoter. After we bred the female heterozygous MRP1.0-DSR rabbit, we were able to determine the tdTomato concentration in the milk from this animal. Milk collected from the MRP1.0-DSR female was brightly red as observed by naked eye, in contrast to the milk from a WT female. We calculated the tdTomato concentration to be 6.3g/L. Later, we measured the tdTomato concentration to be 12.5g/L in a homozygous MRP1.0-DSR female.

Example 8. Integrase Mediated Production of Knock-In Embryos

Figure 8:
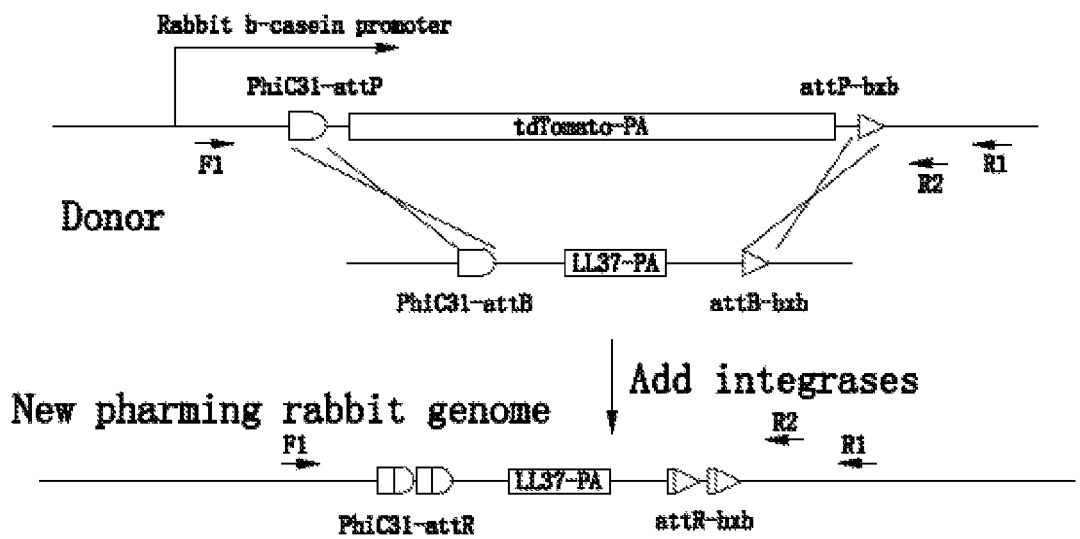
FIG. 8 illustrates the integrase mediated production of LL37 knock-in embryos.

We next used the master rabbits to generate knock-in embryos with target transgene. FIG. 8 illustrates the scheme of integrase mediated knock-in of LL37. As shown in FIG. 8, to generate knock-in embryos with target transgene, e.g., LL37, a donor construct that comprises the target transgene flanked by recombinase recognition sites, e.g., PhiC31-attB and Bxb1-attB, were introduced to the embryos of master rabbits. Also introduced to the embryos were integrases, e.g., PhiC31 and Bxb1, which mediate the recombination between the recombinase recognition sites. As a result, the tdTomato gene was replaced by the target transgene, generating the new pharming rabbit.

The results of integrase mediated production of knock-in embryos are shown in Tables 7 and 8.

TABLE 7

Integrase mediated production of LL37 knock-in embryo

| Genotype of embryos | Embryos injected | Embryos sequenced | LL37 knock-in embryos (%) |
|---|---|---|---|
| Master rabbit (heterozygous) | 9 | 9 | 1(11) |
| WT | 12 | 11 | 0(0) |

TABLE 8

Integrase mediated production of rhRVIIa knock-in embryo

| Genotype of embryos | Embryos injected | Embryos sequenced | FVIIa knock-in embryos (%) |
|---|---|---|---|
| Master rabbit (heterozygous) | 17 | 16 | 3(18) |
| WT | 14 | 14 | 0(0) |

What is claimed is:

1. A method for making a genetically modified rabbit, the method comprising:
   a) introducing into a rabbit embryo:
      i) a Cas protein or a nucleic acid encoding the Cas protein,
      ii) a single guide RNA (sgRNA) that targets the nucleic acid sequence of SEQ ID NO:1, and
      iii) a DNA comprising a first recombinase recognition site (RRS), such that the DNA is inserted into intron 1 of an endogenous β-Casein gene in the rabbit embryo;
   b) transferring the rabbit embryo to a female rabbit; and
   c) generating a genetically modified rabbit whose genome comprises the first RRS in exon 1 of the endogenous β-casein gene from the rabbit embryo obtained in step b).

2. The method of claim 1, further comprising introducing a homology directed repair (HDR) enhancer into the rabbit embryo in step a).

3. The method of claim 2, wherein the HDR enhancer is RS-1.

4. A method for making a transgenic rabbit that is capable of expressing an exogenous protein in its milk, the method comprising:
   d) obtaining an embryo from the genetically modified rabbit generated in step c) of claim 1;
   e) introducing:
      (i) a construct comprising a nucleic acid sequence encoding an exogenous protein and a second RRS, and
      (ii) a recombinase into the embryo obtained in step in step d);
   f) transferring the embryo obtained in step e) to a female rabbit; and
   g) allowing the embryo obtained in step f) to develop into a transgenic rabbit whose genome comprises the nucleic acid sequence encoding the exogenous protein operably linked to an endogenous β-casein promoter and capable of expressing the exogenous protein in milk.

5. The method of claim 4, further comprising:
   h) inducing lactation in the transgenic rabbit obtained in step e); and
   i) collecting said exogenous protein from milk of the transgenic rabbit obtained in step h).

6. The method of claim 4, wherein the nucleic acid sequence encoding the exogenous protein comprises at its 5' end a nucleic acid sequence encoding a signal-peptide.

7. The method of claim of 4, wherein the nucleic acid sequence encoding the exogenous protein comprises at its 3' end a polyA sequence.

8. The method of claim of 4, wherein the exogenous protein is selected from the group consisting of antigen binding proteins, antibodies, vaccines, fusion proteins, enzymes, co-enzymes, clotting factors, and lysosomal proteins.

9. The method of claim of 4, wherein the exogenous protein is human factor VII (FVII) or peptide LL37.

10. The method of claim 1, wherein the recombinase is selected from the group consisting of Cre, Flp, the lambda integrase, gamma-delta resolvase, Tn3 resolvase, Sin resolvase, Gin invertase, Hin invertase, Tn5044 resolvase, IS607 transposase, Bxb1, wBeta, BL3, phiR4, A118, TG1, MR11, phi370, SPBc, TP901-1, phiRV, FC1, K38, phiBT1 and phiC31.

11. The method of claim 1, wherein:
   the DNA further comprises a nucleic acid sequence encoding a reporter protein, flanked by the first RSS and a second RSS,
   the genetically modified rabbit has a genome comprising the nucleic acid sequence encoding the reporter protein operably linked to an endogenous β-casein promoter, and
   expresses the reporter protein in milk.

12. The method of claim 11, wherein the first RRS is phiC31-attP and the second RRS is Bxb1-attP, or vice versa.

* * * * *

UNITED STATES PATENT AND TRADEMARK OFFICE
CERTIFICATE OF CORRECTION

| | |
|---|---|
| PATENT NO. | : 11,647,737 B2 |
| APPLICATION NO. | : 16/475127 |
| DATED | : May 16, 2023 |
| INVENTOR(S) | : Ruby Yanru Tsai et al. |

It is certified that error appears in the above-identified patent and that said Letters Patent is hereby corrected as shown below:

On the Title Page

On left Column, Lines 4-7, the information of item (71) Applicants shall read as:
Applicants: ASC THERAPEUTICS, INC., Milpitas, CA (US); THE REGENTS OF THE UNIVERSITY OF MICHIGAN, Ann Arbor, MI (US)

Signed and Sealed this
Third Day of October, 2023

*Katherine Kelly Vidal*

Katherine Kelly Vidal
*Director of the United States Patent and Trademark Office*

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
```
ggatatcatg ttagagtgcc tgg                                           23

<210> SEQ ID NO 2
<211> LENGTH: 2990
<212> TYPE: DNA
<213> ORGANISM: Oryctolagus cuniculus

<400> SEQUENCE: 2

| | | | | | |
|---|---|---|---|---|---|
| gtaagaattc | taggtatgaa | tttcatttac | tcacccaacc | tttatttcag | aatatgatta | 60 |
| aaatacagtt | tttgaaataa | agttacctaa | gatagtacta | aaattatttt | taacacttag | 120 |
| aaaaaatagg | atgcctagaa | atatttaaca | aaacatacaa | agatcatata | ggccttgtaa | 180 |
| atcctatgca | atgtagtaac | taatttaata | tgtgtagcaa | aactagctaa | tacttaatat | 240 |
| taagatgata | tctatttctt | gaattaaatg | tcttcaaatt | tacataacat | attaaaacca | 300 |
| taaaacaaat | atatttaaat | tagcttgaga | agatgaataa | ttattgggaa | agttttttt | 360 |
| accaatatgt | agcatgctga | gtcaagaaac | agatggaggg | agtgggaaca | tacaatatcc | 420 |
| taaatattca | taaacttttt | agaagaagag | tgtactcatt | aaagttaagt | tgcctagact | 480 |
| ctccagtttc | ccagtttatc | atctagttta | taatatttca | aaataatctt | acaatggaga | 540 |
| catggagata | cagagttaag | ctgaaaaatc | aaattattct | acatttttaag | aaaattctac | 600 |
| atgcgacaaa | gatgtcttgc | aaacaaaaca | caaggaaat | agatgatttg | aaaacagtag | 660 |
| atgtatacca | gtctataata | aaattcttgc | ttaaaaacta | gtatacaaaa | tactacgttt | 720 |
| aagagataga | aaatgcagtg | agattcttct | tactttactt | gtttattgcc | ttgtgttaca | 780 |
| tttttttgaa | ctctttacaa | gaaaaactcc | tttggaaatt | tatggtgtct | caggcaaggt | 840 |
| aaaattaata | aataattata | aaccattcat | aagaaaaaca | aaaaattatt | tcacaaatg | 900 |
| gaattatttc | aaccttcaac | tattggaaag | gatattttc | ttttttttt | aagattcatt | 960 |
| ttatttatca | gaagggcaga | gtttcagaga | gagaggaagg | gaaagacaca | gagagaggtc | 1020 |
| ttctttctgt | tggttcactc | cccaaatagc | tacaatggcc | agggtgggc | caggccaaag | 1080 |
| ccaggaatca | agagcttctc | ctgggtctcc | aatgtgggtg | caggggtcca | agcacttgga | 1140 |
| ccttcctcca | ctgctttccc | agggcattag | catggagctg | gattggaagt | ggagcagtgg | 1200 |
| ggacttaaac | ctgcatccat | gtgggatgcc | catgctgcat | gtagaggctt | aacccaccat | 1260 |
| gccacagcac | tgggcccagg | agatgacagt | tttcagaagc | agaactttat | tctgagaact | 1320 |
| gtttgaattt | cagaaatta | gtttaaaaat | atgaaaatga | agatcgagtg | tcaaatatta | 1380 |
| ttatggcata | aaaattaatt | tttaaaataa | atgatttaaa | atgcaagaaa | aggaaggat | 1440 |
| atttggctta | gtggttaaag | tgctccttag | gatatcatgt | tagagtgcct | ggctttgagt | 1500 |
| cctaatgctg | ctccaactcc | agcttcctgc | taatgcacag | cctgagaggc | aacaggtaat | 1560 |
| ggctcaacta | gttggatacc | tgtcacccag | gtgggaggcc | tgcagtgagt | tcacagctct | 1620 |
| tgaatttgtt | ctgacccagc | cccagccttt | gctggcattt | ggggagtgat | ccaacagata | 1680 |
| ggagttctct | aactgccttt | ctgtcttgtg | tatgtctctc | tgtctttcag | ataaaaaaaa | 1740 |
| aattaaaaat | gcaacaagaa | aatcatagag | gtcatttagt | atattttgat | caaaagtatt | 1800 |
| aacatatatt | tcataagagg | tagcttgggg | ttagggagta | ggcaagagga | agtagccctt | 1860 |
| tgtaagtcat | caagggatca | gtgtgcattt | taatagcaag | agaaggcctg | cgctgcagct | 1920 |
| cactaggcta | atcctccgcc | ttgcggcacc | ggcacactgg | gttctagtcc | cggtcggggc | 1980 |
| gccggattct | gtcctggttg | cccctcttcc | aggccagctc | tctgctgtgg | ccagggagtg | 2040 |
| cagtggagga | tggcccagct | ccttgggccc | tgcaccccat | gggagaccag | gagaagcacc | 2100 |

```
tggctcctgc cttcggatca gcgcggtgcg gcggcggcca ttggagggtg aaccaacgga    2160
aaaggaagac ctttctctct gtctctctct ctctcactgt ccactctgcc tgtcaaaaaa    2220
ataaaataaa aaacccaaag ctctacccgg ctcaagggtg aggaaaaaaa aatagcaaga    2280
gaagcaacct ggagagttat ctctaaaatc acatggcata atgagaagag acatgatttg    2340
gtgtatgggg aggaagacta cacagtgggg acagatggag aaaactcaaa cctatcatct    2400
aaaaaatcat ctggggaatg aagcaaataa aggaaacaac aaatgaaaat ttcagtttca    2460
ttgaaaatga gcagatcaat tcaactagat atgcatggca actgtttggc agaaaaaaat    2520
caaaataaag ggtcaattat aattgtatgc attttcttga tcagttacct gttgtagaat    2580
tgagtctgct ttaggacgaa aatcttatta ttttgctcat tgctgcattc ctagtacctg    2640
gacactgaca atgaaagatg ctaaataaat attttgaat atatgaatca atacatattt    2700
ctgtaaatat tgataacttt atccctttca aaaagtaaag catggtagtg tgagtgagag    2760
agaaaatcag aagcatggag gagagtagtg aaatttgaat tttataccag ggaagatttt    2820
gaatttgatc atctgacaaa acttctttac ttttttacgg tgaagtgcaa gcattttac    2880 tgcattatct tggatgtctt ttaaaggaac actagcccta ctcaagtaaa aacattgacc    2940
tgattgacta attgattgac tgattaattc ccttgtctct ccattcacag                2990
```

```
<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
ggtcctcatt ctcgcctgcc tgg                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
ggtggctctc gctcttgcaa ggg                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
ggggttaggg agtaggcaag agg                                              23

<210> SEQ ID NO 6
<211> LENGTH: 51
<212> TYPE: DNA
<213> ORGANISM: Artificial Sequence
<220> FEATURE:
<223> OTHER INFORMATION: Synthetic

<400> SEQUENCE: 6
ccatcgccta gatcatcaac ccaacttgcc tcttttcagt cgagtttaag g                51
```

```
<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
tcgactgaaa agaggcaagt tgg                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
gcaagttggg ttgatgatct agg                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
cgactgaaaa gaggcaagtt ggg                                              23

<210> SEQ ID NO 10
<211> LENGTH: 34
<212> TYPE: DNA
<213> ORGANISM: Artificial Sequence
<220> FEATURE:
<223> OTHER INFORMATION: Synthetic

<400> SEQUENCE: 10
gtgccagggc gtgcccttgg gctccccggg cgcg                                  34

<210> SEQ ID NO 11
<211> LENGTH: 39
<212> TYPE: DNA
<213> ORGANISM: Artificial Sequence
<220> FEATURE:
<223> OTHER INFORMATION: Synthetic

<400> SEQUENCE: 11
ccccaactgg ggtaaccttt gagttctctc agttggggg                             39

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12
gtgccagggc gtgcccttga gttctcagtt ggggg                                 35

<210> SEQ ID NO 13
<211> LENGTH: 36
<212> TYPE: DNA
<213> ORGANISM: Artificial Sequence
<220> FEATURE:
<223> OTHER INFORMATION: Synthetic
```

<400> SEQUENCE: 13
ccccaactgg ggtaaccttt gggctccccg ggcgcg        36

<210> SEQ ID NO 14
<211> LENGTH: 83
<212> TYPE: DNA
<213> ORGANISM: Artificial Sequence
<220> FEATURE:
<223> OTHER INFORMATION: Synthetic

<400> SEQUENCE: 14
ctatggccgt gatgacctgt gtcttcgtgg tttgtctggt caaccaccgc ggtctcagtg        60
gtgtacggta caaacccagt cga        83

<210> SEQ ID NO 15
<211> LENGTH: 78
<212> TYPE: DNA
<213> ORGANISM: Artificial Sequence
<220> FEATURE:
<223> OTHER INFORMATION: Synthetic

<400> SEQUENCE: 15
ctggccgtgg ccgtgctcgt cctcgtcggc cggcttgtcg acgacggcgg tctccgtcgt        60
caggatcatc cgggccac        78

<210> SEQ ID NO 16
<211> LENGTH: 82
<212> TYPE: DNA
<213> ORGANISM: Artificial Sequence
<220> FEATURE:
<223> OTHER INFORMATION: Synthetic

<400> SEQUENCE: 16
ctggccgtgg ccgtgctcgt cctcgtcggc cggcttgtcg acgacggcgg tctcagtggt        60
gtacggtaca aacccagtcg ac        82

<210> SEQ ID NO 17
<211> LENGTH: 80
<212> TYPE: DNA
<213> ORGANISM: Artificial Sequence
<220> FEATURE:
<223> OTHER INFORMATION: Synthetic

<400> SEQUENCE: 17
ctatggccgt gatgacctgt gtcttcgtgg tttgtctggt caaccaccgc ggtctccgtc        60
gtcaggatca tccgggccac        80

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
cctcattctc gcctgcctgg tgg        23

<210> SEQ ID NO 19
<211> LENGTH: 23
<212> TYPE: DNA
<213> ORGANISM: Artificial Sequence
<220> FEATURE:

```
<223> OTHER INFORMATION: Synthetic

<400> SEQUENCE: 19
cctatagtac aatctcacgg acc                                              23

<210> SEQ ID NO 20
<211> LENGTH: 20
<212> TYPE: RNA
<213> ORGANISM: Artificial Sequence
<220> FEATURE:
<223> OTHER INFORMATION: Synthetic

<400> SEQUENCE: 20
ggauaucaug uuagagugcc                                                  20
```